United States Patent
Belenkaya

(10) Patent No.: US 9,603,970 B2
(45) Date of Patent: Mar. 28, 2017

(54) BIODEGRADABLE SHAPE-MEMORY MATERIAL AND METHOD

(71) Applicant: Bronislava G. Belenkaya, Campbell, CA (US)

(72) Inventor: Bronislava G. Belenkaya, Campbell, CA (US)

(*) Notice: Subject to any disclaimer, the term of this patent is extended or adjusted under 35 U.S.C. 154(b) by 0 days.

(21) Appl. No.: 14/798,422

(22) Filed: Jul. 13, 2015

(65) Prior Publication Data

US 2016/0008510 A1    Jan. 14, 2016

Related U.S. Application Data

(60) Provisional application No. 62/023,790, filed on Jul. 11, 2014.

(51) Int. Cl.
| | | |
|---|---|---|
| *A61L 27/26* | (2006.01) | |
| *A61L 27/58* | (2006.01) | |
| *C08L 39/06* | (2006.01) | |
| *C08L 67/04* | (2006.01) | |
| *A61L 15/00* | (2006.01) | |

(52) U.S. Cl.
CPC .............. *A61L 27/26* (2013.01); *A61L 27/58* (2013.01); *A61L 2400/16* (2013.01)

(58) Field of Classification Search
CPC .......... A61L 27/26; A61L 27/58; C08L 39/06; C08L 67/04; C08L 2201/12; C08L 2201/06
USPC ........................................................ 525/185
See application file for complete search history.

(56) References Cited

U.S. PATENT DOCUMENTS 2,699,054 A * 1/1955 Conover ................ A61K 31/65
                                                        552/203
7,309,498 B2 * 12/2007 Belenkaya ........ A61F 13/00042
                                                        424/443

* cited by examiner

*Primary Examiner* — Fred M Teskin

(57) ABSTRACT

A biodegradable material with shape retention ability may be prepared using a process that includes (a) dissolving a polymer that in a first solvent to obtain a first solution; (b) dissolving a poly-N-vinyl lactam (e.g., polyvinyl pyrrolidone (PVP)) in a second solvent to obtain a second solution; (c) mixing the first solution with the second solution to obtain a liquid mixture; and (d) preparing the biodegradable material using the liquid mixture in an electrospinning process. The polymer may include a copolymer of lactide and caprolactone, where the lactide preferably includes L-lactide. The first solution may be an aprotic solvent, preferably ethyl acetate.

21 Claims, No Drawings

BIODEGRADABLE SHAPE-MEMORY MATERIAL AND METHOD

CROSS REFERENCE TO RELATED APPLICATIONS

This application relates to and claims priority of U.S. provisional patent application ("Provisional Application"), Ser. No. 62/023,790, entitled "Biodegradable Shape-Memory Material and Method," filed on Jul. 11, 2014. The disclosure of the Provisional Application is hereby incorporated by reference in its entirety.

BACKGROUND OF THE INVENTION

1. Field of the Invention

The present invention relates to biodegradable materials. In particular, the present invention relates to biodegradable materials that return to their original shapes even after being stretched by a relatively significant amount.

2. Discussion of the Related Art

There has been great interest in the use of biodegradable materials for tissue regeneration use. One proposed application, for example, is the use of biodegradable arterial and venal vascular grafts. The biodegradable vascular graft would replace or bypass a damaged native blood vessel until the body's tissue regeneration mechanism regenerates new vascular tissue to replace the degrading vascular graft. To be successful, the vascular graft needs to be compatible and, preferably, promote cell attachment and provide a habitable environment for the growing new tissue. In addition, because the pressure in the circulatory system changes between the systolic pressure and the diastolic pressure within each heartbeat, the vascular graft is preferable flexible, i.e., without permanent deformation as a result of the higher systolic pressure.

Another proposed application for biodegradable materials, for example, is to provide support for an implanted prosthetic tissue or device, such as a breast implant or a pacemaker. An artificial prosthetic tissue made of biodegradable material would provide support to the implanted prosthetic tissue or device until the body's tissue regeneration mechanism replaces the degrading artificial prosthetic tissue with new connective tissue. Until then, the artificial prosthetic tissue needs to be flexible to avoid permanent deformation due to forces resulting from the patient's normal activities, such as normal ambulatory activities and exercise. For that application, the prosthetic tissue preferably should promote cell attachment and cell growth necessary for regeneration of the native connective tissue.

Therefore, a biodegradable material with shape-retention abilities ("shape memory") and which promotes cell attachment and growth is desired.

SUMMARY

According to one embodiment of the present invention, a biodegradable hydrophilic material with shape retention ability may be prepared using a process that includes (a) dissolving a polymer that includes a hydrophobic, biodegradable polymer in a first solvent to obtain a first solution; (b) dissolving a poly-N vinyl lactam (e.g., polyvinylpyrrolidone (PVP)) in a second solvent to obtain a second solution; (c) mixing the first solution with the second solution to obtain a liquid mixture; and (d) preparing the biodegradable material using the liquid mixture in an electrospinning process. The polymer may include a copolymer of lactide and caprolactone, where the lactide preferably includes L-lactide. The first solution may be an aprotic solvent, preferably ethyl acetate. The second solvent may include absolute ethanol. In one embodiment, the ratio of the polymer to the solvent is selected between approximately 60-90% by weight, preferably 60-80% by weight, and the ratio of PVP to absolute ethanol is between approximately 5-25% by weight, preferably 10-20% by weight. The PVP is preferably low molecular weight (e.g., less than 20,000 daltons) and more particularly 1000-4000 daltons. In that embodiment, the quantities of the first and second solutions are determined such that the resulting mixture has a ratio of the polymer to PVP of approximately 3:1 to 8:1 by weight, preferably 5:1 by weight.

According to one embodiment of the present invention, a semi-transparent, apparently single-phase mixture is accomplished by adding the second solution in small aliquots into the first solution under stirring and at an elevated temperature maintained between 30° C. to 50° C., preferably about 40° C. The solution is then processed electro-hydrodynamically (e.g., by electrospinning) into a biodegradable material. The resulting biodegradable material has a surprising shape memory property with a glass transition temperature of 22° C., thereby allowing the shape memory property to exist at normal human body temperature.

The present invention is better understood upon consideration of the detailed description below.

DETAILED DESCRIPTION OF THE PREFERRED EMBODIMENTS

Biodegradable materials that include a blend of polyvinylpyrrolidone (PVP) and a biodegradable polymer (e.g., polylactide) using an electrospinning process are hydrophilic, even though the polymer may itself be hydrophobic. Such a biodegradable material is disclosed, for example, in U.S. Pat. No. 7,309,498 to Belenkaya et al., entitled "Biodegradable Absorbents and Methods of Preparation," issued on Dec. 10, 2007. Although an explanation of the hydrophilicity has not been found in the literature of the prior art, the present inventor believes that hydrophilicity in such electrospun materials result from molecular level mixing of a hydrophobic polymer and a poly-N-vinyl lactam. Examples of suitable hydrophobic polymers include homopolymers or copolymers of L(−), D(+), d,l-lactide with glycolide, caprolactone, p-dioxanon, homopolymers or copolymers of caprolactone with L(−)-lactide, or D(+), or d,l-lactide, or glycolide, or p-dioxanon, and copolymers of L(−), or D(+), or d,l-lactide, or caprolactone, or p-dioxanon with polyoxyethylene glycols (PEG), or homopolymers or copolymers of p-dioxanon, and mixtures any of the homopolymers or copolymers. Examples of Poly-N-vinyl lactams include homopolymers or copolymers of N-vinyl pyrrolidone, N-vinyl butyrolactam, and N-vinyl caprolactam, or up to about 15-20 weight percent of one or more of other vinyl monomers copolymerizable with the N-vinyl lactams, such as acrylic acid, acryl amides or hydroxyalkylacrylates. Of the poly (N-vinyl) lactam homopolymers, the poly(N-vinyl) pyrrolidone (PVP) homopolymers of molecular weight 40,000 or less are preferred. A variety of poly (N-vinyl) pyrrolidones are commercially available. It is believed that in a molecular mixture of the hydrophobic polymer with PVP, with the oxygen atom in the PVP participates in hydrogen bonding in an environment where water or hydroxyl-containing molecules are present. For further promotion of the blend components assembly multifunctional hydroxyl species (e.g., those containing small or polymeric molecules or alcohols) may be added to the polymer blend solution. Example of such small or polymeric molecules include glycerol, mannitol, sorbitol, inositol, starch, polyoxyethylene glycol derivatives, pluronics, castor oil, or other molecules. A hydrophilic biodegradable material is preferred in tissue regeneration applications (e.g., in a synthetic extracellular matrix), as hydrophilicity is believed to promote cell attachment. Furthermore, a bio-mimicking hydrophilic material is even more preferred.

Electrospun materials are also preferred in these applications, as electrospinning processes provide the advantage of allowing the size of the resulting fibers to be tuned by suitably varying certain process parameters, such as solution concentration, and electric field strength. Fiber sizes between ten nanometers to ten microns or greater may be obtained in this manner. In addition, especially those that deliver the polymer mixture using compressed gas, some electrospinning processes allow tuning the resulting material density and pore size by varying the pressure of delivery. Pore sizes of tens of microns may be prepared in this manner. The electrospinning process forms compatible mixtures from a blend of incompatible components (e.g., hydrophilic PVP and hydrophobic PLC). It is believed that electrospinning allows immediate evaporation of the solvents, while 'freezing' (i.e., preserving) the molecular structures achieved in the solution.

By combining these tuning techniques, the present inventor has created a number of hydrophilic biodegradable materials that have fiber sizes, internal pore sizes and material densities similar to those of native extracellular matrices have been created. In particular, a blend of PVP and a polymer including caprolactone has been shown to have "shape memory" characteristic that allows the resulting biodegradable material to have all the characteristics desired for tissue regeneration, as discussed above. Such materials find numerous applications, such as a wound dressing, as antimicrobial agents (e.g., antibiotics, such as silver sulfadiazine) may be provided, for example, by electrospraying on the surface of a substrate.

One application of the materials the present invention is as a hemostatic material, or a material that can be platelet-enriched to become a plasma-enriched plasma-like material. In particular, when compounds containing the divalent calcium ion (i.e, $Ca^{++}$) (e.g., $CaCl_2$, Calcium gluconate, calcium acetate, calcium benzoate, calcium formate, or calcium nitrate) are incorporated into or onto the fiber via an electrospraying process, or by simply soaking the fabric in an aqueous solution of the corresponding calcium salt or mixture. The preferable concentration of $Ca^{++}$ salts in solution is between 0.1% w/w to 10% w/w to total polymer components weight.

EXAMPLE 1

A polymer including caprolactone, such as a copolymer of polylactide and caprolactone is mixed in liquid with PVP. The PVP may be of molecular weight up to 20,000 daltons, more preferably 1200-4000 daltons. The polymer may be provided in a solution using, for example, an aprotic solvent (e.g., ethyl acetate). PVP may also be added in liquid phase using a protic solvent, such as ethanol, preferably absolute alcohol. The mixture is then used in an electrospinning process to produce sheet samples or tubular samples in dimensions, densities, pore sizes, and fiber sizes suitable for tissue regeneration applications.

EXAMPLE 2

A copolymer of lactide (preferably, poly-L-lactide) and caprolactone was dissolved, at least 60% by weight, in ethyl acetate and mixed with a second solution that includes PVP, at least 5% by weight, in absolute ethanol. The amount of the second solution provided was such that the resulting mixture contains a ratio between 3:1 and 8:1 by weight of the copolymer to PVP. The resulting liquid mixture appeared to be two-phase, including a gel-phase. The liquid mixture was stirred while being provided in an electrospinning process to produce sheet samples or tubular samples in dimensions, densities, pore sizes, and fiber sizes suitable for tissue regeneration applications.

EXAMPLE 3

A copolymer of lactide (preferably, poly-L-lactide) and caprolactone (PLC) was dissolved, 70-80% by weight, in ethyl acetate and mixed with a second solution that includes PVP, about 10-20% by weight (preferably 15-20% by weight) in absolute ethanol. The amount of the second solution provided was such that the resulting mixture contains an about 5:1 ratio by weight of the copolymer to PVP. The ethanol solution containing the PVP was provided in small aliquots (e.g., drop-by-drop) with stirring into the solution containing the lactide-caprolactone copolymer, which was maintained at 40° C. Unlike the mixture of Example 2 above, the resulting liquid mixture treated in this example appeared to be single-phase, appearing as a semi-transparent solution. The liquid mixture was provided in an electrospinning process to produce sheet samples or tubular samples in dimensions, densities, pore sizes, and fiber sizes suitable for tissue regeneration applications.

A sample of the material prepared under the conditions of Example 3 was found to absorb an amount of water that is 600% of its own weight. The water absorbing ability was demonstrated to be retained after the sample was repeatedly hydrated and dried five or more times. An unexpected property of this sample is shape retention. A fast shape recovery after stretching, bending, twisting or any other deformation has been observed. In one experiment, a 150 microns thick, 4 cm by 6 cm sample was stretched at room temperature (e.g., 25° C.) lengthwise by 35% from its unstretched state. Upon release of the stretching force, the sample returned to its unstretched state within 30 seconds. The sample was found to have a glass transition temperature ($T_G$) of 22° C. This glass transition temperature for the sample is indeed surprising as the glass transition temperatures of polycarpolactone and poly-L-lactide are about −60° C. and 60-65° C., respectively. At normal body temperature of 36.5° C.-40° C., a glass transition temperature of 22° C. means that the sample's shape memory property is available for tissue regeneration applications.

EXAMPLE 4

A blend including PVP and a copolymer of PLC may be provided as an electrospun coating over a flat or tubular substrate (e.g., a PLC film), which may also be prepared by electrospinning.

EXAMPLE 5

To promote the mixing or interaction between PVP and a poly-caprolactone containing polymer, multifunctional alcohols such as mannitol, sorbitol, inositol, starch, polyoxyethylene glycol derivatives, pluronics, castor oil, or other molecules may be added to the PVP-ethanol solution, wherein the ratio of PVP to the multifunctional alcohol is between 95:5% by weight, and preferably 98:2% by weight.

The above detailed description is provided to illustrate the specific embodiments of the present invention and is not intended to be limiting. Numerous modifications and variations within the scope of the present invention are possible. The present invention is set forth in the accompanying claims.

I claim:

1. A method for preparing a biodegradable material with shape retention ability, comprising:
dissolving a biodegradable hydrophobic polymer in a first solvent to obtain a first solution;
dissolving a poly-N-vinyl lactam in a second solvent to obtain a second solution, the poly-N-vinyl lactam having a molecular weight between 1000-4000 daltons, wherein the poly-N-vinyl lactam comprises poly-N vinyl pyrrolidone (PVP);
mixing the first solution with the second solution to obtain a liquid mixture; and
preparing the biodegradable material using the liquid mixture in an electrospinning process.

2. The method of claim 1, wherein the biodegradable, hydrophobic polymer comprises a copolymer of lactide and caprolactone.

3. The method of claim 1, wherein the biodegradable, hydrophobic polymer is selected from the group consisting of homopolymers or copolymers of L(−), D(+), d,l-lactide with glycolide, caprolactone, p-dioxanon, homopolymers or copolymers of caprolactone with L(−)-lactide, or D(+), or d,l-lactide, or glycolide, or p-dioxanon, and copolymers of L(−), or D(+), or d,l-lactide, or caprolactone, or p-dioxanon with polyoxyethylene glycols (PEG), or homopolymers or copolymers of p-dioxanon, and mixtures any of the homopolymers or copolymers.

4. The method of claim 1, wherein the poly-N-vinyl lactam is selected from the group consisting of homopolymers or copolymers of N-vinyl pyrrolidone, N-vinyl butyrolactam, and N-vinyl caprolactam, or up to about 15-20 weight percent of one or more of other vinyl monomers copolymerizable with the N-vinyl lactams.

5. The method of claim 1, wherein the first solvent comprises an aprotic solvent.

6. The method of claim 5, wherein the aprotic solvent comprises ethyl acetate.

7. The method of claim 6, wherein the ratio of the polymer to the aprotic solvent is between 60-80% by weight.

8. The method of claim 1, wherein the second solvent comprises absolute ethanol, wherein the ratio of poly-N vinyl lactam to absolute ethanol is between 10-20% by weight.

9. The method of claim 8, wherein the mixture comprises a ratio of the polymer to Poly-N-vinyl lactam of 3:1 to 9:1 by weight.

10. The method of claim 8, wherein the biodegradable, hydrophobic polymer comprises a poly-caprolactone containing polymer, the method further comprises providing a multifunctional alcohol selected from the group consisting of mannitol, sorbitol, inositol, starch, polyoxyethylene glycol derivatives, pluronics, and castor oil, into the second solvent.

11. The method of claim 1, wherein the mixing is accomplished by adding the second solution in aliquots into the first solution under stirring.

12. The method of claim 1, wherein the mixture is maintained between 30° C. to 50° C.

13. A biodegradable material with shape retention ability, provided in accordance with a method that comprises:
dissolving a polymer that includes polycaprolactone in a first solvent to obtain a first solution;
dissolving polyvinylpyrrolidone (PVP) in absolute ethanol to obtain a second solution, the PVP having a molecular weight between 1000-4000 daltons;
mixing the first solution with the second solution in aliquots to obtain a liquid mixture at an elevated temperature; and
preparing the biodegradable material using the liquid mixture in an electrospinning process.

14. The biodegradable material of claim 13, wherein the polymer comprises a copolymer of lactide and caprolactone.

15. The biodegradable material of claim 13, wherein the first solvent comprises an aprotic solvent.

16. The biodegradable material of claim 15, wherein the aprotic solvent comprises ethyl acetate.

17. The biodegradable material of claim 16, wherein the ratio of the solvent to the polymer is between 60-80% by weight.

18. The biodegradable material of claim 13, wherein the ratio of PVP to absolute ethanol is between 15-20% by weight.

19. The biodegradable material of claim 18, wherein the mixture comprises a ratio of the polymer to PVP of 3:1 to 9:1 by weight.

20. The biodegradable material of claim 13, wherein the elevated temperature is maintained between 30° C. to 50° C.

21. The biodegradable material of claim 13, wherein the biodegradable material incorporate a calcium salt.

* * * * *